United States Patent
Jadhav et al.

(10) Patent No.: US 11,857,680 B2
(45) Date of Patent: *Jan. 2, 2024

(54) COMPOSITION OF DOCETAXEL LIPOSOMAL INJECTION WITH HIGH DRUG LOADING

(71) Applicant: SHILPA MEDICARE LIMITED, Raichur (IN)

(72) Inventors: Kiran K Jadhav, Bangalore (IN); Prashanth S, Bangalore (IN); Shivakumar Pradeep, Visianagaram (IN); Sreenivasa Reddy, Bangalore (IN)

(73) Assignee: SHILPA MEDICARE LIMITED, Karnataka (IN)

( * ) Notice: Subject to any disclaimer, the term of this patent is extended or adjusted under 35 U.S.C. 154(b) by 225 days.

This patent is subject to a terminal disclaimer.

(21) Appl. No.: 17/073,437

(22) Filed: Oct. 19, 2020

(65) Prior Publication Data

US 2022/0117892 A1   Apr. 21, 2022

Related U.S. Application Data

(63) Continuation of application No. 16/480,308, filed as application No. PCT/IB2018/059280 on Nov. 26, 2018.

(51) Int. Cl.
| | |
|---|---|
| A61K 9/127 | (2006.01) |
| A61K 31/337 | (2006.01) |
| A61K 47/26 | (2006.01) |
| A61K 47/24 | (2006.01) |
| A61K 47/28 | (2006.01) |
| A61K 9/00 | (2006.01) |

(52) U.S. Cl.
CPC ............ *A61K 9/127* (2013.01); *A61K 9/0019* (2013.01); *A61K 9/1277* (2013.01); *A61K 31/337* (2013.01); *A61K 47/24* (2013.01); *A61K 47/26* (2013.01); *A61K 47/28* (2013.01)

(58) Field of Classification Search
None
See application file for complete search history.

(56) References Cited

U.S. PATENT DOCUMENTS

| | | | |
|---|---|---|---|
| 8,591,942 B2 | 11/2013 | Javeri et al. | |
| 8,912,228 B2 | 12/2014 | Palepu | |
| 9,655,846 B2 | 5/2017 | Javeri et al. | |
| 2007/0178147 A1* | 8/2007 | Desai | A61K 9/1277 424/450 |
| 2008/0166403 A1 | 7/2008 | Wang et al. | |
| 2016/0310600 A1* | 10/2016 | Ali | A61K 47/24 |

FOREIGN PATENT DOCUMENTS

| | | | | |
|---|---|---|---|---|
| CN | 101991538 B | 9/2013 | | |
| WO | 2014167435 A2 | 10/2014 | | |
| WO | WO-2019106511 A1 * | 6/2019 | | A61K 47/26 |

OTHER PUBLICATIONS

Theranostic liposomes of TPGS coating for targeted co-delivery of docetaxel and quantum dots, Muthu et al.; Biomaterials. Apr. 2012;33(12):3494-501.

* cited by examiner

*Primary Examiner* — Gollamudi S Kishore

(74) *Attorney, Agent, or Firm* — Benesch, Friedlander, Coplan & Aronoff LLP

(57) ABSTRACT

The present invention relates to a pharmaceutical liposomal composition comprising of about 0.8% w/w to about 1% w/w of docetaxel, about 30% w/w to about 38% w/w of Soya Phosphatidyl Choline, about 0.2% w/w to about 0.8% w/w of Sodium Cholesteryl Sulfate, about 61% w/w to about 68% w/w of Sucrose and a pH adjusting agent, wherein the pH of liposomal composition is less than 3.5 and the process for preparation thereof.

5 Claims, No Drawings

COMPOSITION OF DOCETAXEL LIPOSOMAL INJECTION WITH HIGH DRUG LOADING

FIELD OF THE INVENTION

The present invention relates to Docetaxel liposomes for injection which will be used to target the tumour site. It relates to increase the drug's residence time in blood. The present invention also includes to achieve more than 90% drug loading using combination of various solvents.

BACKGROUND OF THE INVENTION

Docetaxel is an antineoplastic agent belonging to the taxoid family being marketed by Sanofi-Aventis under trade name Taxotere®. It is prepared by semi synthesis beginning with a precursor extracted from the renewable needle biomass of yew plants. The chemical name for docetaxel is (2R,3S)—N-carboxy-3-phenylisoserine, N-tert-butyl ester, 13-ester with 5beta-20-epoxy-1,2α,4,7β,10β,13α-hexahydroxytax-11-en-9-one 4-acetate 2-benzoate, trihydrate. Docetaxel has the following structural formula:

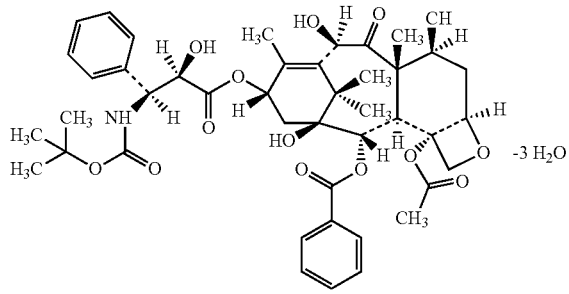

Docetaxel binds to free tubulin and promotes the assembly of microtubules, which reduces the availability of tubulin for, and thereby prevents, cell division. Simultaneously, docetaxel inhibits microtubule disassembly, causing apoptosis. See Taxotere® Prescribing Information.

Docetaxel is marketed as Taxotere®, which is FDA-approved for breast cancer, non-small cell lung cancer, hormone refractory prostate cancer, gastric adenocarcinoma, and squamous cell carcinoma of head and neck cancer. Taxotere is available as a sterile solution of docetaxel in a sealed vial, i.e., a single-vial injection concentrate, containing 20 mg/mL docetaxel; 0.54 g/mL polysorbate 80, and 0.395 g/mL dehydrated alcohol solution. For administration to patients, an amount of Taxotere injection concentrate is injected into a 250 mL infusion bag or bottle of either 0.9% sodium chloride solution or 5% dextrose solution to produce a final concentration of 0.3 to 0.74 mg/ml. The recommended therapy is six cycles of docetaxel given once every three weeks. See id.

The presence of polysorbate 80 in Taxotere, however, most often results in serious side effects. Such reactions characterized by generalized rash/erythema, hypotension and/or bronchospasm, or very rarely fatal anaphylaxis, have been reported in patients. Hypersensitivity reactions require immediate discontinuation of the Taxotere infusion and administration of appropriate therapy.

In order to reduce the side effects induced by polysorbate 80, patients are treated with dexamethasone for three days prior to therapy. Dexamethasone is a steroid that suppresses the immune response in patients, which can be especially detrimental in cancer patients under chemotherapy, whose immunity may already be compromised due to the destruction of healthy cells by the chemotherapeutic treatment. As a result, these patients can be susceptible to bacterial and fungal infections. Further, despite receiving the recommended 3-day dexamethasone premedication, patients still report hypersensitivity side effects from Taxotere.

Due to these side effects, most of the patients stop Taxotere therapy by the end of the second or third cycle, skip a dose, or continue further therapy at a reduced dose. Similarly, other solubilizing agents such as CREMOPHOR EL®, which is a polyethoxylated castor oil used in connection with the marketed paclitaxel product TAXOL®, induce similar allergic reactions requiring premedication with a steroid.

Recently, D-a-tocopheryl PEG 1000 succinate (TPGS), derivative of vitamin E has been successfully utilized in numerous drug carrier formulations like micro emulsions, micelles, glycerosomes, nanoparticles and solid dispersions. It is a FDA approved excipient with hydrophilic polar head and hydrophobic non polar alkyl chain prepared by esterification of vitamin E by polyethylene glycol of molecular weight 1000 D. Principally, it is used as solubilizer, emulsifier and vehicle in lipidic formulations. The recent application of TPGS includes oral absorption enhancer owing to P-gp efflux inhibition, promoting cell uptake and drug absorption. Furthermore, TPGS provide better membrane stabilizing effect to the lipid bilayer as compared to PEGs owing to better hydrophilic lipophilic balance in the molecule.

U.S. Pat. No. 8,591,942 discloses the method of preparing liposomes containing docetaxel, the method consisting of dispersing soy phosphatidylcholine and sodium oleate in an aqueous medium to produce dispersed liposomes.

U.S. Pat. No. 9,655,846 discloses the suspension of liposomes in an aqueous medium, the liposomes encapsulating and solubilizing docetaxel at a concentration of at least about 5 mg docetaxel per ml of the aqueous medium.

U.S. Pat. No. 8,912,228 discloses the sterile pharmaceutical formulation for use in treatment of a patient in need thereof, comprising docetaxel or a pharmaceutically acceptable salt thereof, one or more solubilizers, α-lipoic acid, TPGS, one or more hydrotropes, and optionally one or more agents having a $pK_a$ of about 3 to about 6.

US Application No. US20080166403 discloses the long circulating liposome, comprising a phospholipid bilayer and a hydrophilic core, wherein the phospholipid bilayer contains vitamin E derivative (D-alpha tocopheryl polyethylene glycol 1000 succinate, TPGS).

PCT Patent Publication No. WO2014167435A2 discloses the surface functionalized liposomal formulation comprising an anticancer agent as an active ingredient, liposomes surrounded by a functional coating of D-a-Tocopheryl Polyethylene Glycol 1000 Succinate (TPGS), wherein the anticancer agent is entrapped within the liposomes, and further wherein said formulation has an encapsulation efficiency of >70%.

CN Patent No. 101991538 discloses the use of a TPGS-containing liposome composition in preparation of drug-loaded liposomes.

Muthu et al.; Biomaterials. 2012 April; 33(12):3494-501 recently disclosed the TPGS coated liposomes for brain delivery of docetaxel prepared by solvent injection method. The reported formulations posed about 64.10±0.57% encapsulation efficiency which was significantly lower than the present invention (encapsulation efficiency-83.63±1.16%).

The probable reasons for this appreciation of encapsulation efficiency in the present invention could be attributed to the exhaustive optimization of the various process parameters, composition of excipients and method of preparation of the liposomes. The same group in further extension of work improved the therapeutic efficacy of the docetaxel by combination therapy with quantum dots. However, the present invention does not inculcate any such combination therapy.

However, there exists a need to develop a docetaxel liposomal injection formulation is needed to avoid these side effects, premedication requirements, and patient noncompliance issues associated with the currently marketed formulation of Taxotere.

SUMMARY OF THE INVENTION

In one object, the present invention provides herein, liposomal injection compositions consisting essentially of a therapeutically effective amount of docetaxel and an excipient that facilitates intravenous administration, and which will be used to target the tumour site. It relates to increase the drug's residence time in blood. The present invention also includes to achieve more than 90% drug loading using combination of various solvents, preferably methanol and tertiary butanol (T-butanol or tertiary butyl alcohol) in ratio of 1:1.

In another object, the present invention further provides the docetaxel liposomal injection consisting essentially of docetaxel, phospholipids, cholesterol, lyoprotectant and a pH adjusting agent.

Definition of Selected Terms

In describing and claiming the present invention, the following terminologies will be used in accordance with the definitions set out below.

The term "liposomes" are vesicles composed of one or more concentric lipid bilayers which contain an entrapped aqueous volume. The bilayers are composed of two lipid monolayers having a hydrophobic "tail" region and a o hydrophilic "head" region, where the hydrophobic regions orient toward the center of the bilayer and the hydrophilic regions orient toward the inner or outer aqueous phase.

As used herein in connection with numerical values, the terms "about" mean+/−10% of the indicated value, including the indicated value.

DETAILED DESCRIPTION OF THE INVENTION

The present invention provides herein, compositions consisting essentially of a therapeutically effective amount of docetaxel and an excipient that facilitates intravenous administration, and which will be used to target the tumour site. It relates to increase the drug's residence time in blood. The present invention also includes to achieve more than 90% drug loading using combination of various solvents, preferably methanol and tertiary butanol (T-butanol or tertiary butyl alcohol) in ratio of 1:1.

In a preferred embodiment, the pharmaceutical composition of the invention is liposomal injection.

In the most preferred embodiment, the pharmaceutical liposomal injection composition comprises docetaxel and pharmaceutically acceptable excipients.

Docetaxel, preferably used in the present pharmaceutical liposomal composition is of about 0.8% w/w to about 1% w/w based on the total weight of the composition. The preferred concentration of docetaxel in composition is about 0.85% w/w to about 0.95% w/w based on the total weight of the composition. Most preferably, the docetaxel is used in the composition of about 0.9% w/w based on total weight of the composition.

In further embodiment, the pharmaceutical liposomal composition comprises docetaxel, phospholipids, cholesterol, lyoprotectant and a pH adjusting agent, wherein the pH of liposomal composition is less than 3.5.

In yet another embodiment, the present invention further provides the docetaxel liposomal composition comprising docetaxel, phospholipids, cholesterol, solubilizer, lyoprotectant, and a pH adjusting agent.

Examples of the phospholipids are selected form the group consisting of a natural phospholipid, a synthetic phospholipid, and combinations thereof. Lecithin is one of the natural resources for phospholipid. Lecithin is a mixture found in egg yolk and soya. It comprises a number of phospholipids including phosphatidylcholine (PC, Soya Phosphatidyl Choline), phosphatidylethanolamine (PE), and phosphatidylinositol (PI). Natural phospholipids also include, e.g. soy phosphatidyl choline (SPC), sphingomyelin, and phosphatidylglycerol (PG). Synthetic phospholipids include, but are not limited to, derivatives of phosphocholine (for example, DDPC, DLPC, DMPC, DPPC, DSPC, DOPC, POPC, DEPC), derivatives of phosphoglycerol (for example, DMPG, DPPG, DSPG, POPG, DSPG-NA, DSPG-NH4), derivatives of phosphatidic acid (for example, DMPA, DPPA, DSPA), derivatives of phosphoethanolamine (for example, DMPE, DPPE, DSPE DOPE), derivatives of phosphoserine (for example, DOPS), PEG derivatives of phospholipid (for example, mPEG-phospholipid, mPEG 2000-DSPE, polyglycerin-phospholipid, functionalized-phospholipid, and terminal activated-phospholipid) and any mixtures thereof. Preferably, phospholipid is selected from soy phosphatidyl choline (SPC) and mixture phospholipids are selected from soy phosphatidyl choline (SPC) and N-Carbonylmethoxypolyethylenglycol-2000)-1, 2-distearoyl-sn-glycero-3-phosphoethanolamine (MPEG2000-DSPE). Phospholipids preferably used in the pharmaceutical liposomal composition of present invention is Soya Phosphatidyl Choline. Soya Phosphatidyl Choline used in the present invention is from about 30% w/w to about 40% w/w based on the total weight of the composition, preferably from about 30% w/w to about 38% w/w based on the total weight of composition, even more preferably, of about 31% w/w to about 36% w/w based on total weight of the composition and most preferably of about 32% w/w based on the total weight of the composition.

Examples of the cholesterol is selected from the group consisting of cholesterol, cholesteryl sulfate and its salts (e.g., sodium salt), cholesteryl hemisuccinate, cholesteryl succinate, cholesteryl oleate, polyethylene glycol derivatives of cholesterol (cholesterol-PEG), coprostanol, cholestanol, cholestane, cholic acid, cortisol, corticosterone, hydrocortisone and calciferol. Preferably, the cholesterol is selected from Sodium Cholesteryl Sulfate. Sodium Cholesteryl sulfate is preferably used in the range from about 0.2% w/w to about 0.8% w/w based on the total weight of the composition, more preferably, of about 0.4% w/w to about 0.6% w/w based on total weight of the composition, and most preferably of about 0.5% w/w based on total weight of composition.

Examples of the solubilizer is selected from the group consisting vitamin E TPGS, polyethylene glycol (PEG) 400, and propylene glycol (PG) tween 80, tween 20, glycerol span 80 and glycofurol. Preferably, the solubilizer is selected from vitamin E TPGS. Solubilizer preferably used in the pharmaceutical liposomal injection composition of about 0.1% to about 1.5% based on the total weight of the composition.

Examples of the lyoprotectant are selected from the group consisting of sucrose, trehalose, arabinose, erythritol, fructose, galactose, glucose, lactose, maltitol, maltose, maltotriose, mannitol, mannobiose, mannose, ribose, sorbitol, saccharose, xylitol, xylose, dextran, or a mixture thereof. Preferably, the lyoprotectant is selected from sucrose. Sucrose preferably used in the pharmaceutical liposomal composition is about 61% to about 68% based on the total weight of the composition, more preferably of about 62% to about 66% based on total weight of the composition and most preferably of about 66.5% w/w based on the total weight of composition.

Examples of pH adjusting agents used in the present liposomal composition is hydrochloric acid. pH adjusting agent is used to adjust the pH of the liposomal composition to about less than pH 3.5, more preferably pH of about 3. The inventors of the present invention have surprisingly found that with the pH of less than 3.5, there was high drug loading of more than 90% docetaxel into liposomes (more 90% of docetaxel is encapsulated into liposomes as bound drug and less than about 10% of docetaxel is present as free drug).

In embodiments of the present invention, the present invention provides a pharmaceutical liposomal composition comprising of about 0.8% w/w to about 1% w/w of docetaxel, about 30% w/w to about 38% w/w of Soya Phosphatidyl Choline, about 0.2% w/w to about 0.8% w/w of Sodium Cholesteryl Sulfate, about 61% w/w to about 68% w/w of Sucrose and a pH adjusting agent, wherein the pH of liposomal composition is less than 3.5.

In further embodiment of the present invention, the present invention provides a pharmaceutical liposomal composition consisting essentially of about 0.8% w/w to about 1% w/w of docetaxel, about 30% w/w to about 38% w/w of Soya Phosphatidyl Choline, about 0.2% w/w to about 0.8% w/w of Sodium Cholesteryl Sulfate, about 61% w/w to about 68% w/w of Sucrose and a pH adjusting agent, wherein the pH of liposomal composition is less than 3.5.

In another embodiment of the present invention, the present invention provides a pharmaceutical liposomal composition consisting of about 0.8% w/w to about 1% w/w of docetaxel, about 30% w/w to about 38% w/w of Soya Phosphatidyl Choline, about 0.2% w/w to about 0.8% w/w of Sodium Cholesteryl Sulfate, about 61% w/w to about 68% w/w of Sucrose and a pH adjusting agent, wherein the pH of liposomal composition is less than 3.5.

In specific embodiment, the present invention provides a pharmaceutical liposomal composition comprising of about 0.9% w/w of docetaxel, about 32% w/w of Soya Phosphatidyl Choline, about 0.5% w/w of Sodium Cholesteryl Sulfate, about 66.5% w/w of Sucrose and a pH adjusting agent, wherein the pH of liposomal composition is about 3.

In another embodiment, the present invention provides a pharmaceutical liposomal composition consisting essentially of about 0.9% w/w of docetaxel, about 32% w/w of Soya Phosphatidyl Choline, about 0.5% w/w of Sodium Cholesteryl Sulfate, about 66.5% w/w of Sucrose and a pH adjusting agent, wherein the pH of liposomal composition is about 3.

In further embodiment, the present invention provides a pharmaceutical liposomal composition consisting essentially of about 0.9% w/w of docetaxel, about 32% w/w of Soya Phosphatidyl Choline, about 0.5% w/w of Sodium Cholesteryl Sulfate, about 66.5% w/w of Sucrose and a pH adjusting agent, wherein the pH of liposomal composition is about 3.

In specific embodiment, the present invention provides a pharmaceutical liposomal composition comprising of about 0.9% w/w of docetaxel, about 32% w/w of Soya Phosphatidyl Choline, about 0.5% w/w of Sodium Cholesteryl Sulfate, about 66.5% w/w of Sucrose and a pH adjusting agent, wherein the pH of liposomal composition is of about 2.5 to about 3.2.

In another embodiment, the present invention provides a pharmaceutical liposomal composition consisting essentially of about 0.9% w/w of docetaxel, about 32% w/w of Soya Phosphatidyl Choline, about 0.5% w/w of Sodium Cholesteryl Sulfate, about 66.5% w/w of Sucrose and a pH adjusting agent, wherein the pH of liposomal composition is of about 2.5 to about 3.2.

In further embodiment, the present invention provides a pharmaceutical liposomal composition consisting essentially of about 0.9% w/w of docetaxel, about 32% w/w of Soya Phosphatidyl Choline, about 0.5% w/w of Sodium Cholesteryl Sulfate, about 66.5% w/w of Sucrose and a pH adjusting agent, wherein the pH of liposomal composition is of about 2.5 to about 3.2.

The pharmaceutical liposomal composition of present invention comprises the liposomes of $d_{90}$ less than 200 nm, $d_{50}$ less than 150 nm and $d_{10}$ less than 100 nm.

The docetaxel liposomes of the present invention are prepared by a process comprising the steps of comprising the steps of:
a. dispersing Soya Phosphatidyl Choline in solvent mixture to solubilize Soya Phosphatidyl Choline;
b. adding sodium cholesteryl sulfate to the solubilized Soya Phosphatidyl Choline;
c. adding docetaxel to contents of step b;
d. preparing sucrose solution by dissolving sucrose in purified water and adding the pH adjusting agent to form the sucrose solution, wherein the pH of sucrose solution is about 3.
e. adding contents of step c to step d and mixing with high hear at 8000 RPM for 15 minutes
f. rota evaporation;
g. addition of pH adjusting agent to pH of about 3;
h. extrusion of liposomes containing docetaxel to the particle size $d_{90}$ of less than 200 nm;
i. filtration and
j. lyophilization.

Examples of the solvents are selected from the group consisting of methanol, ethanol (anhydrous alcohol), propanol, butanol (t-butanol, tertiary butyl alcohol), chloroform, isoamyl alcohol, isopropanol, 2-methoxy ethanol, Tetrahydrofuran, DMSO acetone, acetonitrile and any combinations thereof. The solvents preferably used for the preparation of liposomal composition is tertiary butyl alcohol and methanol in the ratio of 1:1.

In a preferred embodiment, the present invention relates to the method of preparing liposomal composition comprising the steps of:
a. dispersing Soya Phosphatidyl Choline in solvent mixture of methanol and tertiary butyl alcohol to solubilize Soya Phosphatidyl Choline
b. adding sodium cholesteryl sulfate to the solubilized Soya Phosphatidyl Choline;
c. adding docetaxel to contents of step b;

d. preparing sucrose solution by dissolving sucrose in purified water and adding the pH adjusting agent to form the sucrose solution, wherein the pH of sucrose solution is about 3.
e. adding contents of step c to step d and mixing with high hear at 8000 RPM for 15 minutes
f. rota evaporation;
g. addition of pH adjusting agent to pH of about 3;
h. extrusion of liposomes containing docetaxel to the particle size $d_{90}$ of less than 200 nm;
i. filtration and
j. lyophilization.

In a more preferred embodiment, the present invention relates to the method of preparing liposomal composition comprising the steps of:
a. dispersing Soya Phosphatidyl Choline in solvent mixture of methanol and tertiary butyl alcohol in the ratio of 1:1 to solubilize Soya Phosphatidyl Choline;
b. adding sodium cholesteryl sulfate to the solubilized Soya Phosphatidyl Choline;
c. adding docetaxel to contents of step b;
d. preparing sucrose solution by dissolving sucrose in purified water and adding the pH adjusting agent to form the sucrose solution, wherein the pH of sucrose solution is about 3.
e. adding contents of step c to step d and mixing with high hear at 8000 RPM for 15 minutes
f. rota evaporation;
g. addition of pH adjusting agent to pH of about 3;
h. extrusion of liposomes containing docetaxel to the particle size $d_{90}$ of less than 200 nm;
i. filtration and
j. lyophilization.

In another embodiment liposomal docetaxel liquid filtrate is lyophilized by comprising the steps of freezing the filtrate at temperature ranging from about −5° C. to about −50° C. for the time duration ranging from about 10 hours to about 20 hours; drying under vacuum at a temperature ranging from about −50° C. to about 40° C. for time duration ranging from about 40 hours to about 80 hours.

In a further specific embodiment liposomal docetaxel liquid filtrate is lyophilized by comprising the steps of
a. Loading the filtrate filled vials at −5° C.±2° C.;
b. Freezing the filtrate formulation at −5° C.±2° C. for 100 minutes±20 minutes
c. Maintaining the freezing temperature for another 300 minutes±20 minutes
d. Reducing the temperature up to −25° C.±2° C. for 50 minutes±10 minutes
e. Maintaining the reduced temperature for another 90 minutes±10 minutes
f. Reducing the temperature up to −50° C.±2° C. for 60 minutes±10 minutes
g. Maintaining the reduced temperature for another 300 minutes±10 minutes
h. Evacuating the filtrate by creating vacuum of 750 m Torr to obtain frozen formulation
i. Drying the frozen formulation at −50° C.±2° C. by creating vacuum at 750 m Torr for 30 minutes±10 minutes
j. Drying the frozen formulation at −35° C.±2° C. by creating vacuum at 400 m Torr for 120 minutes±10 minutes
k. Maintaining the drying for another 1255 minutes±20 minutes at −35° C.±2° C. and 400 m Torr vacuum.
l. Drying the frozen formulation at −25° C.±2° C. by creating vacuum at 300 m Torr for 150 minutes±10 minutes
m. Maintaining the drying for another 600 minutes±20 minutes at −25° C.±2° C. and 300 m Torr vacuum.
n. Drying the frozen formulation at −5° C.±2° C. by creating vacuum at 200 m Torr for 150 minutes±10 minutes
o. Maintaining the drying for another 900 minutes±20 minutes at −5° C.±2° C. and 200 m Torr vacuum.
p. Drying the frozen formulation at 20° C.±2° C. by creating vacuum at 100 m Torr for 150 minutes±10 minutes
q. Maintaining the drying for another 300 minutes±20 minutes at 20° C.±2° C. and 100 m Torr vacuum.
r. Drying the frozen formulation at 25° C.±2° C. by creating vacuum at 100 m Torr for 30 minutes±10 minutes
s. Maintaining the drying for another 150 minutes±20 minutes at 25° C.±2° C. and 100 m Torr vacuum.
t. Drying the frozen formulation at 40° C.±2° C. by creating vacuum at 100 m Torr for 30 minutes±10 minutes
u. Maintaining the drying for another 120 minutes±20 minutes at 40° C.±2° C. and 100 m Torr vacuum
v. Drying the frozen formulation at 25° C.±2° C. by creating vacuum at 100 m Torr for 30 minutes±10 minutes
w. Maintaining the drying for another 60 minutes±20 minutes at 25° C.±2° C. and 100 m Torr vacuum.

In the embodiments of the present invention, the lyophilized composition of present invention is administered intravenously to the patients for the treatment of breast cancer, Non-small cell lung cancer, Castration resistant prostate cancer, gastric adenocarcinoma and Squamous Cell Carcinoma of the Head and Neck Cancer.

In embodiments of the invention for intravenous administration, the lyophilized composition is reconstituted with purified water and further diluted with either 0.9% sodium chloride solution or 5% dextrose solution.

In embodiments of the invention the docetaxel liposomal composition of present invention is used for the treatment of breast cancer, Non-small cell lung cancer, Castration resistant prostate cancer, gastric adenocarcinoma and Squamous Cell Carcinoma of the Head and Neck Cancer, wherein the pre-medication with prednisone is not required.

In embodiments of the invention the recommended dose of liposomal composition of present invention is 60 mg/m$^2$ to 100 mg/m$^2$ administered intravenously over 1 hour every 3 weeks.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Examples 1 to 3

Liposomal injection with the following compositions are prepared.

| Ingredients | Example 1 (% w/w) | Example 2 (% w/w) | Example 3 (% w/w) |
|---|---|---|---|
| Docetaxel anhydrous | 0.84%-1% | 0.84%-0.87% | 0.84%-0.87% |
| Soya Phosphatidyl Choline | 30%-38% | 30%-38% | 30%-38% |
| Sodium Cholesteryl Sulfate | 0.2%-0.8% | 0.2%-0.8% | 0.2%-0.8% |
| MPEG2000-DSPE (N-(Carbonylmethoxy-polyethylenglycol-2000)-1,2-distearoyl-sn-glycero-3-phosphoethanolamine) | — | 0.5%-2% | — |
| Vitamin E TPGS | — | — | 0.5%-1.5% |
| Sucrose | 61%-68% | 61%-68% | 61%-68% |
| Solvent mixture | Q.S | Q.S | Q.S |
| 0.1N Hydrochloric acid as pH adjuster | Q.S | Q.S | Q.S |

These Liposomal injections are prepared as follows:

1. Prepare solvent mixture of solubilization of Lipids and Drug by mixing 50:50 v/v of Methanol and T-Butanol mixture.
2. To 4 mL of the solvent mixture of step 1, add and solubilize, weighed quantity of Soya Phosphatidyl Choline, at 60-65° C.
3. To the Lipid solution of step 2, add and solubilize, weighed quantity of Sodium Cholesteryl Sulfate, at 60-65° C.
4. To the Lipid solution of step 3, add and solubilize, weighed quantity of MPEG 2000 DSPE/Vitamin E TPGS, at 60-65° C. (optionally).
5. To the Lipid mixture of step 4, add and solubilize, weighed quantity of Docetaxel at 60-65° C.
6. Mix the contents of step 4 for 10 minutes at 60-65° C. for uniform binding of docetaxel with the lipids.
7. Prepare sucrose solution by dissolving the weighed quantity of sucrose in purified water equivalent to 75% of the batch size.
8. Prepare 0.1 N Hydrochloric acid by diluting the required quantity of 37% concentrated HCl.
9. Adjust the pH of the sucrose solution prepared in the step 7 between pH 3.0 to 4.0 using the 0.1N HCl.
10. Heat the Sucrose solution of step 8 to 60-65° C.
11. Add the Drug Lipid Mixture to Sucrose solution under High Shear Mixing at 5000-20000 RPM by Ethanol Injection method and rinse the container containing Lipid Drug mixture with 1 mL of Solvent Mixture and run the mixture for 2 to 30 minutes.
12. Volume was made up to the mark of the liposomal formulation of step 11, with purified water and if required pH was adjusted to between 3.0 to 4.0.
13. Size reduction of liposomal formulation of step 12, was done using extrusion with 400 nm, 200 nm, 100 nm and 50 nm polycarbonate filters.
14. Post size reduction, the liposomal formulation is sterile filtered using 0.22-micron filter.
15. Post sterile filtration, the samples are freeze dried to get the dry liposomal cake for Injection.

Example 4

| Ingredients | Example 4 (% w/w) |
|---|---|
| Docetaxel anhydrous | 0.91 |
| Soya Phosphatidyl Choline | 32.05 |
| Sodium Cholesteryl Sulfate | 0.5 |
| Sucrose | 66.54 |
| Methanol | Q.S |
| Tertiary butyl alcohol | Q.S |
| 0.1N Hydrochloric acid as pH adjuster | Q.S to pH 3 |
| Purified water | Q.S |

Process for Preparation of Liposomes Encapsulated with Docetaxel:

1. 14.46 g (32.05% w/w) of soya phosphatidyl choline was dispersed in 8 mL of solvent mixture (4 mL of tertiary butyl alcohol and 4 mL of methanol in ratio of 1:1) and mixed with magnetic stirrer in water bath at 47° C. for 25 minutes to solubilize soya phosphatidyl choline.
2. To the solubilized sodium phosphatidyl choline solution of step 1, 226.6 mg (0.5% w/w) of sodium cholesteryl sulfate was added and solubilised with magnetic stirrer in water bath at 49° C. for 45 minutes to form the dispersed liposomes.
3. To the contents of step 3, 412.1 mg (0.91% w/w) of solid docetaxel anhydrous was added and solubilized with magnetic stirrer in water bath at 46° C. for 10 minutes to form docetaxel containing dispersed liposomes.
4. The contents of step 3, as added to sucrose solution (sucrose solution was prepared by dissolving 30.02 g [66.54% w/w] of sucrose in required quantity of purified water with magnetic stirrer in water bath at 45° C. for 2 minutes and further pH is adjusted to 2.7 using 0.1N hydrochloric acid solution) using high shear mixing ultra-turrax T-25 digital at 8000 RPM for 15 minutes.
5. The contents of step 4, was subjected to rota evaporation with chiller temperature of 2° C., bath temperature of 46° C. with vacuum.
6. After rota evaporation, to contents of step 5, required quantity of purified water was added and pH was adjusted to 3 using 0.1N hydrochloric acid solution.
7. The contents of step 6, was extruded with 200 nm, 100 nm, 80 nm and 50 nm polycarbonate membranes using lipex extruder at 47° C. Three cycles of passing resulted in a liposome with particle size d90 of less than 200 nm (i.e 178 nm), d50 of less than 150 nm (i.e 113 nm) and d10 of less than 100 nm (i.e 73 nm)
8. The contents of step 7, was filtered using 0.2 μm membrane filter.
9. The filtrate of step 8, was filled into 30 mL moulded vials and lyophilized using the following lyo cycle.
   a. Loading the filtrate filled vials at −5° C.±2° C.;
   b. Freezing the filtrate formulation at −5° C.±2° C. for 100 minutes±20 minutes
   c. Maintaining the freezing temperature for another 300 minutes±20 minutes
   d. Reducing the temperature up to −25° C.±2° C. for 50 minutes±10 minutes
   e. Maintaining the reduced temperature for another 90 minutes±10 minutes f. Reducing the temperature up to −50° C.±2° C. for 60 minutes±10 minutes
g. Maintaining the reduced temperature for another 300 minutes±10 minutes
h. Evacuating the filtrate by creating vacuum of 750 m Torr to obtain frozen formulation
i. Drying the frozen formulation at −50° C.±2° C. by creating vacuum at 750 m Torr for 30 minutes±10 minutes
j. Drying the frozen formulation at −35° C.±2° C. by creating vacuum at 400 m Torr for 120 minutes±10 minutes
k. Maintaining the drying for another 1255 minutes±20 minutes at −35° C.±2° C. and 400 m Torr vacuum.
l. Drying the frozen formulation at −25° C.±2° C. by creating vacuum at 300 m Torr for 150 minutes±10 minutes
m. Maintaining the drying for another 600 minutes±20 minutes at −25° C.±2° C. and 300 m Torr vacuum.
n. Drying the frozen formulation at −5° C.±2° C. by creating vacuum at 200 m Torr for 150 minutes±10 minutes
o. Maintaining the drying for another 900 minutes±20 minutes at −5° C.±2° C. and 200 m Torr vacuum.
p. Drying the frozen formulation at 20° C.±2° C. by creating vacuum at 100 m Torr for 150 minutes±10 minutes
q. Maintaining the drying for another 300 minutes±20 minutes at 20° C.±2° C. and 100 m Torr vacuum.
r. Drying the frozen formulation at 25° C.±2° C. by creating vacuum at 100 m Torr for 30 minutes±10 minutes
s. Maintaining the drying for another 150 minutes±20 minutes at 25° C.±2° C. and 100 m Torr vacuum.
t. Drying the frozen formulation at 40° C.±2° C. by creating vacuum at 100 m Torr for 30 minutes±10 minutes
u. Maintaining the drying for another 120 minutes±20 minutes at 40° C. 2° C. and 100 m Torr vacuum
v. Drying the frozen formulation at 25° C.±2° C. by creating vacuum at 100 m Torr for 30 minutes±10 minutes
w. Maintaining the drying for another 60 minutes±20 minutes at 25° C.±2° C. and 100 m Torr vacuum.

Comparative Example 1

| Ingredients | Comparative Example 1 (% w/w) |
|---|---|
| Docetaxel anhydrous | 0.91 |
| Soya Phosphatidyl Choline | 32.05 |
| Sodium Cholesteryl Sulfate | 0.5 |
| Sucrose | 66.54 |
| Methanol | Q.S |
| Ethanol | Q.S |
| 0.1N Hydrochloric acid as pH adjuster | Q.S to pH 4 |
| Purified water | Q.S |

The process for preparation is same as that of Example 4, with the changes in solvent mixture of Methanol and Ethanol in ratio of 1:1, pH of 4, without rota evaporation process (step 5) and change in lyophilization cycle (without 40° C. drying step t and u).

Comparative Example 2

| Ingredients | Comparative Example 2 (% w/w) |
|---|---|
| Docetaxel anhydrous | 0.91 |
| Soya Phosphatidyl Choline | 32.05 |
| Sodium Cholesteryl Sulfate | 0.5 |
| Sucrose | 66.54 |
| Methanol | Q.S |
| Tertiary butyl alcohol | Q.S |
| 0.1N Hydrochloric acid as pH adjuster | Q.S to pH 4.5 |
| Purified water | Q.S |

The process for preparation is same as that of Example 4, with the changes in pH of formulation adjusted to 4.5

Comparative Example 3

| Ingredients | Comparative Example 3 (% w/w) |
|---|---|
| Docetaxel anhydrous | 0.91 |
| Soya Phosphatidyl Choline | 32.05 |
| Sodium Cholesteryl Sulfate | 0.5 |
| Sucrose | 66.54 |
| Methanol | Q.S |
| Tertiary butyl alcohol | Q.S |
| 0.1N Hydrochloric acid as pH adjuster | Q.S to pH 3 |
| Purified water | Q.S |

The process for preparation is same as that of Example 4, with change in lyophilization cycle (without 40° C. drying step t and u).

Example 5: Free Drug, Entrapped Drug, Assay, pH, Residual Solvents of Example-4, Comparative Example 1, 2 & 3

| Test | Example 4 | Comparative Ex.1 | Comparative Ex.2 | Comparative Ex.3 |
|---|---|---|---|---|
| Free Drug | 11.1% | 29.1% | 56.3% | 8.8% |
| Entrapped Drug | 94.8% | 63.7% | 47.3% | 88.1% |
| Assay | 103.6% | 93.5% | 103.3% | 96.0% |
| pH | 3.1 | 4.1 | 4.7 | 3 |
| Residual Solvents | | | | |
| Methanol | 384 ppm | — | — | 1766 ppm |
| T-Butanol | 741 ppm | — | — | 5672 ppm |
| Ethanol | — | — | — | — |

For the measurement of pH, the lyophilized vial of inventive example 4 was reconstituted with purified water to produce 2 mg/mL liposomal formulation of docetaxel.

The Free Drug, Entrapped Drug, Assay of docetaxel liposomal formulation was performed by HPLC and Residual Solvent analysis was performed by Gas chromatography as per the available literature to the personal skilled in the art.

The inventors of present invention have surprisingly found that the example 4 formulation has high drug loading efficiency (about 95%) with the solvents of methanol and tertiary butanol in the ratio of 1:1, rota evaporated, with the formulation pH of about 3 and further the residual solvents (methanol and tertiary butanol) are less (within the limits of 1CH) in comparison to comparative example 1 (containing solvent mixture of ethanol and methanol in ratio of 1:1 at pH of 4.1), comparative example 2 (containing methanol and T-butanol in ratio of 1:1 at pH of 4.7) and comparative example 3 (containing methanol and T-butanol in ratio of 1:1 at pH of 3, without the drying step at 40° C. in lyophilization step t and u of example 4).

The invention claimed is:

1. A pharmaceutical liposomal composition consisting of comprising
   (a) about 0.8% w/w to about 1% w/w of docetaxel,
   (b) about 30% w/w to about 38% w/w of Soya Phosphatidyl Choline,
   (c) about 0.2% w/w to about 0.8% w/w of Sodium Cholesteryl Sulfate,
   (d) about 61% w/w to about 68% w/w of Sucrose and
   (e) a pH adjusting agent,
      wherein the pH of liposomal composition is less than 3.5 and wherein the liposomal composition is prepared by a process of dispersing Soya Phosphatidyl Choline in solvent mixture of methanol and tertiary butanol in the ratio of 1:1.

2. The pharmaceutical liposomal composition of claim 1, wherein the pH of liposomal composition is about 3.

3. The pharmaceutical liposomal composition of claim 1, wherein d90 of liposomes is less than 200 nm.

4. The pharmaceutical liposomal composition of claim 1, wherein the composition comprises of about 0.9% w/w of docetaxel, about 32% w/w of Soya Phosphatidyl Choline, about 0.5% w/w of Sodium Cholesteryl Sulfate and of about 66.5% w/w of Sucrose.

5. A pharmaceutical liposomal composition consisting of
   (a) about 0.8% w/w to about 1% w/w of docetaxel,
   (b) about 30% w/w to about 38% w/w of Soya Phosphatidyl Choline,
   (c) about 0.2% w/w to about 0.8% w/w of Sodium Cholesteryl Sulfate,
   (d) about 61% w/w to about 68% w/w of Sucrose and
   (e) a pH adjusting agent,
      wherein the pH of liposomal composition is less than 3.5.

* * * * *